United States Patent [19]
Li

[11] Patent Number: 5,651,144
[45] Date of Patent: Jul. 29, 1997

[54] JOCKSTRAP FOR CONDOM

[76] Inventor: Yin-Sheng Li, 4th Fl., No. 563, Ta Yu Road, Tao-Yuan City, Taiwan

[21] Appl. No.: 649,330

[22] Filed: May 21, 1996

[51] Int. Cl.$^6$ .................................................. A41B 9/02
[52] U.S. Cl. .................................................. 2/403; 602/70
[58] Field of Search .................... 2/400, 403; 602/68, 602/67, 69–73

[56] References Cited

U.S. PATENT DOCUMENTS

| | | | |
|---|---|---|---|
| 847,779 | 3/1907 | Jarrett | 602/70 |
| 1,020,588 | 3/1912 | West | 602/70 |
| 1,030,224 | 6/1912 | Bauer | 602/70 |
| 1,284,632 | 11/1918 | Fine | 602/70 |
| 3,547,117 | 12/1970 | Smithers | 602/70 |
| 5,003,972 | 4/1991 | Kestler | 602/70 |

FOREIGN PATENT DOCUMENTS

| | | | |
|---|---|---|---|
| 68741 | 6/1958 | France | 602/69 |

*Primary Examiner*—C. D. Crowder
*Assistant Examiner*—Gloria Hale
*Attorney, Agent, or Firm*—Morton J. Rosenberg; David I. Klein

[57] ABSTRACT

A jockstrap for fixing the position of a condom includes a waistband made of soft material. The rear portion and side portions of the waistband are provided with hook-and-loop fastener portions. A pouch portion is attached to the front portion of the waistband and extends to the rear portion of the waistband. A circular slot is provided at the front portion of the pouch portion in correspondence with the position of a user's penis. A tough seam is provided between the pouch portion and the circular slot. An adjusting strap is provided at the rear portion of the pouch portion in correspondence to a hook-and-loop fastener portion of the waistband. By this arrangement, the condom can be fixed onto the user's penis without being peeling off during intercourse.

2 Claims, 6 Drawing Sheets

JOCKSTRAP FOR CONDOM

BACKGROUND OF THE INVENTION

This invention relates to a jockstrap. More particularly, this invention relates to a jockstrap to prevent a condom from peeling off during intercourse.

With the advent of advanced methods of transportation, our modern world has become a global village. Contacts between people from different nations or countries are more and more frequent. Frankly speaking, geographic boundaries have become more and more vague, especially with respect to some diseases. For example, the AIDS virus, which is also called "20th century's pest", has expanded from a local area to the entire world. Right now, there are not any effective measures that can be taken with respect to precautions as well as with respect to medical treatment. The government or hygienic authorities can only ask that people abstain from intercourse with potentially high risk people and to use a condom. Accordingly, using a condom during intercourse has become the only effective measure against the spread of AIDS.

FIG. 1 shows a conventional condom 3, which is widely used by a male during intercourse. It should be noted that when the condom is sleeved onto the penis, there is still a slack 32 between the condom 3 and the penis. Further, the bottom/opening 31 of the condom 3 cannot provide sufficient contraction to fix the condom on the root of the penis. Consequently, the condom can peel off during intercourse. In light of this, without suitable protection provided by the condom, the user may readily get AIDS or other diseases during intercourse.

SUMMARY OF THE INVENTION

It is the object of this invention to provide a jockstrap to solve the problems encountered with conventional condoms.

It is another object of this invention to provide a jockstrap which provides for an intact and conformable contact of a condom with a user's penis, without the possibility of the condom peeling off during intercourse.

It is still another object of this invention to provide a jockstrap which functions as a girdle, as well as help in the erection of the penis.

DETAILED DESCRIPTION OF THE PREFERRED EMBODIMENT

Figure 1:
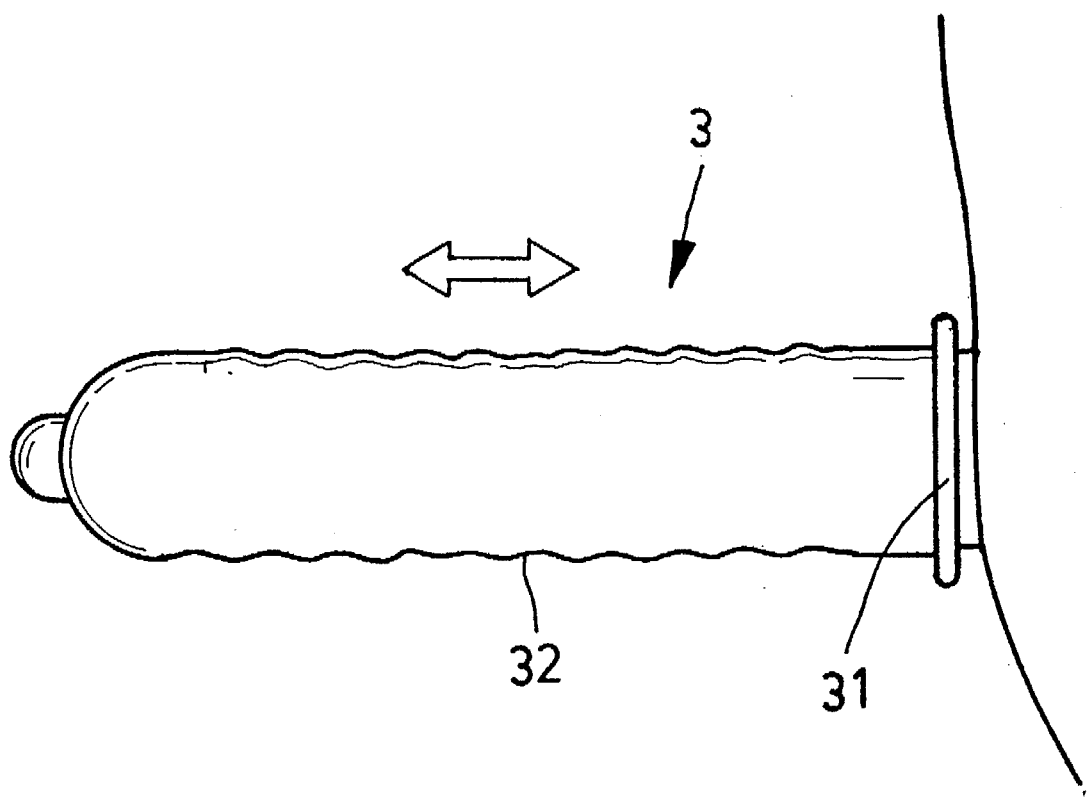
FIG. 1 is an illustration showing usage of a conventional condom.
Figure 2:
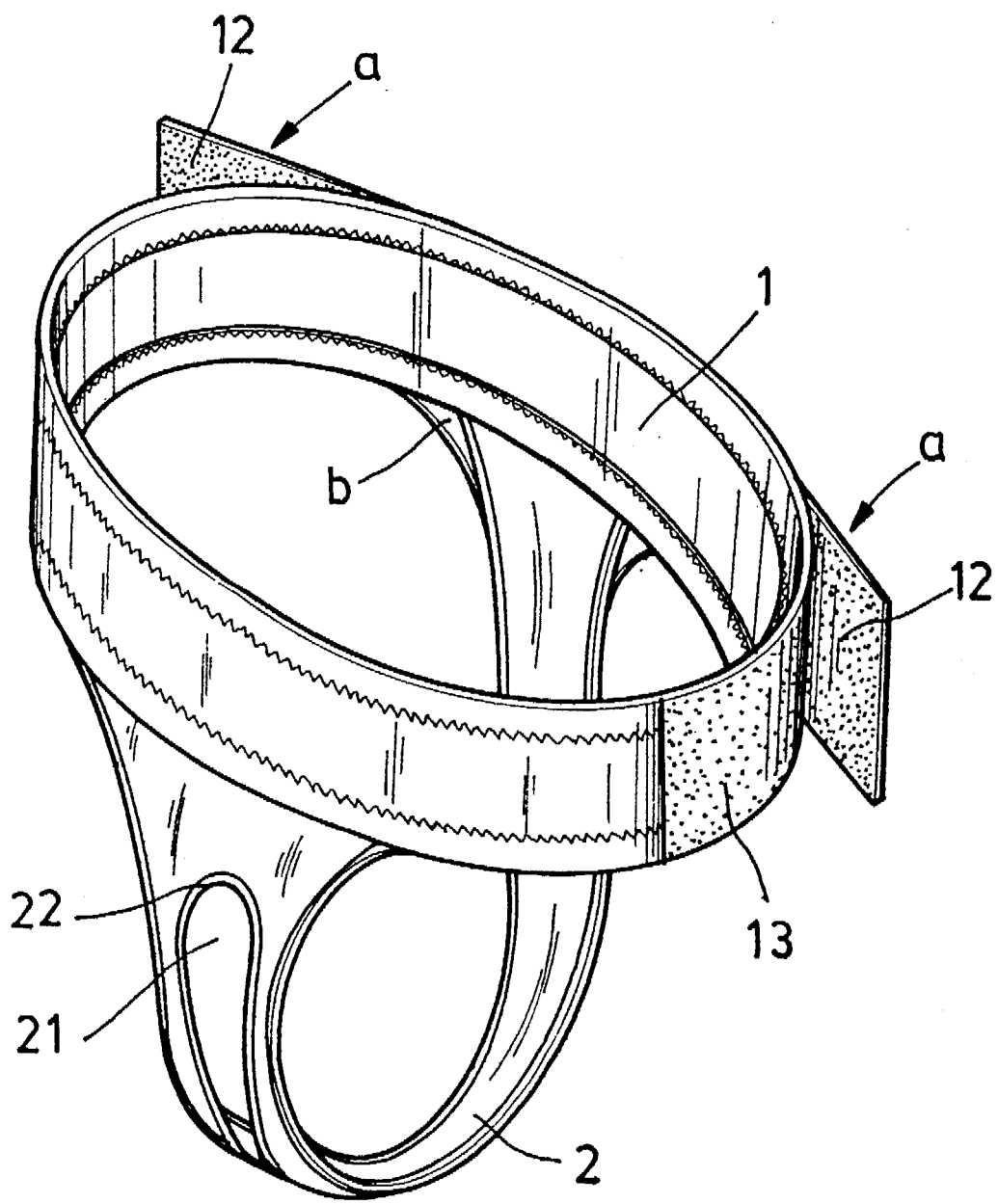
FIG. 2 is a front perspective view of the jockstrap made according to the present invention.
Figure 3:
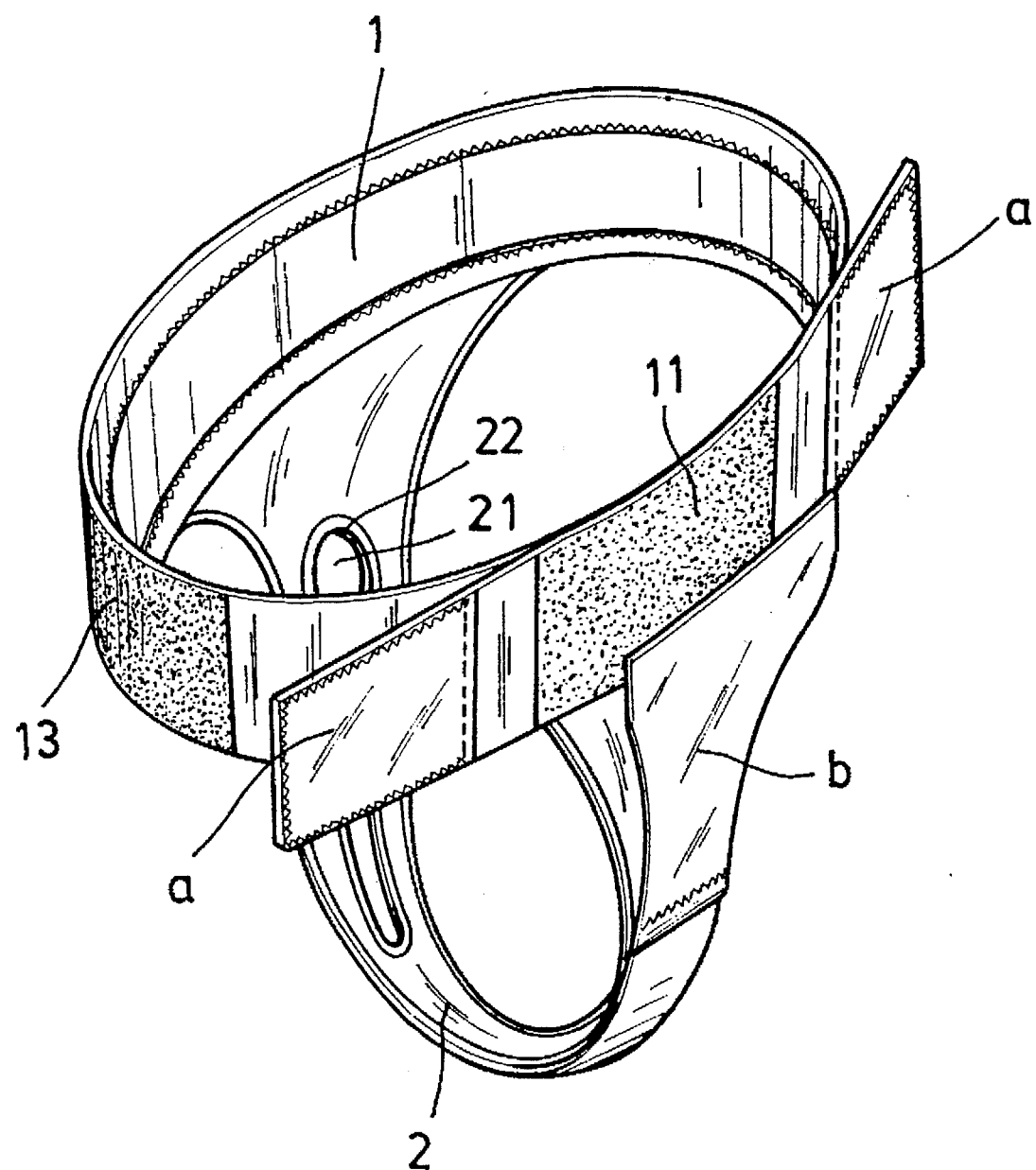
FIG. 3 is a rear perspective view of the jockstrap made according to the present invention.
Figure 4:
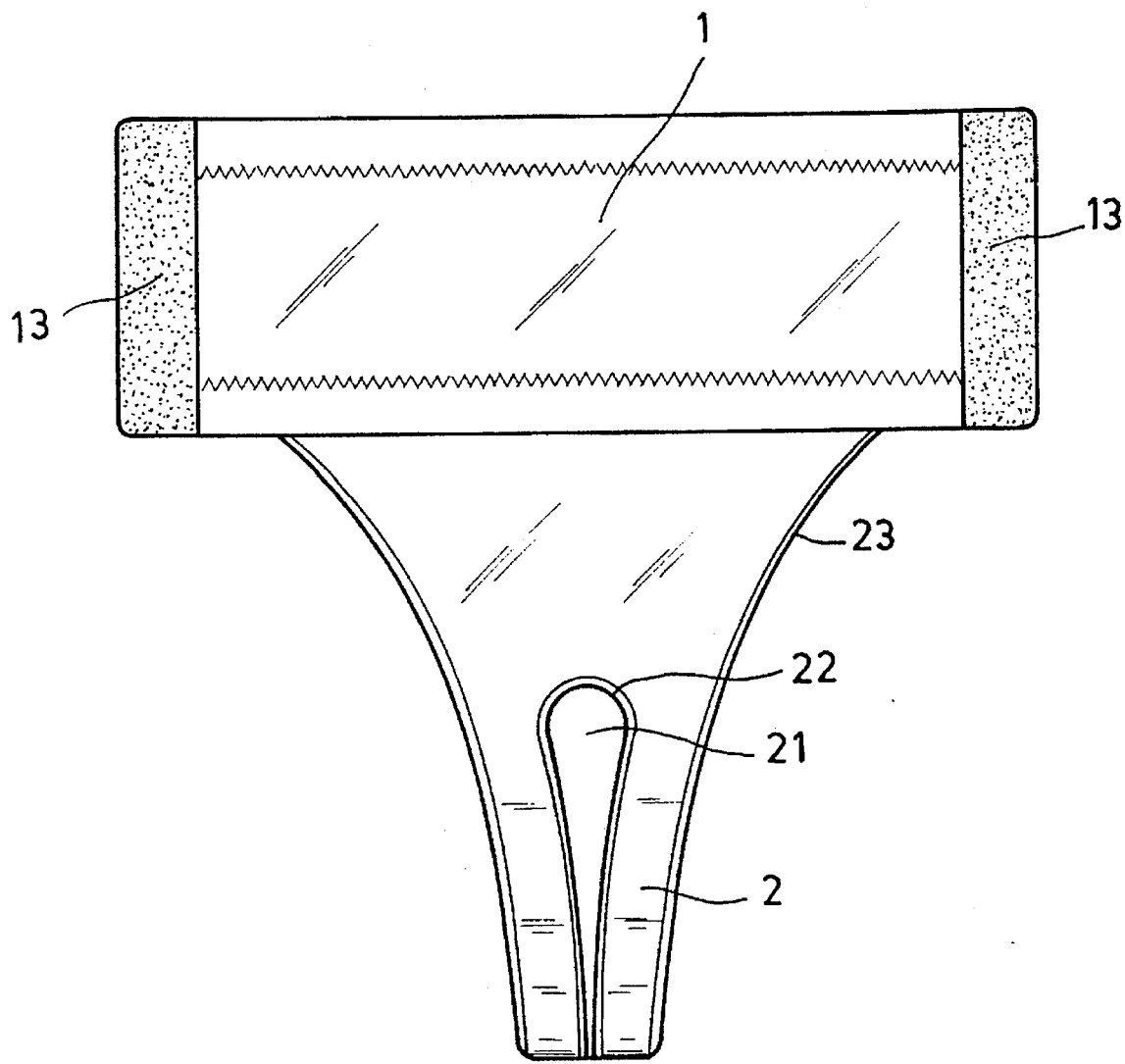
FIG. 4 is a front elevational view of the jockstrap made according to the present invention.
Figure 5:
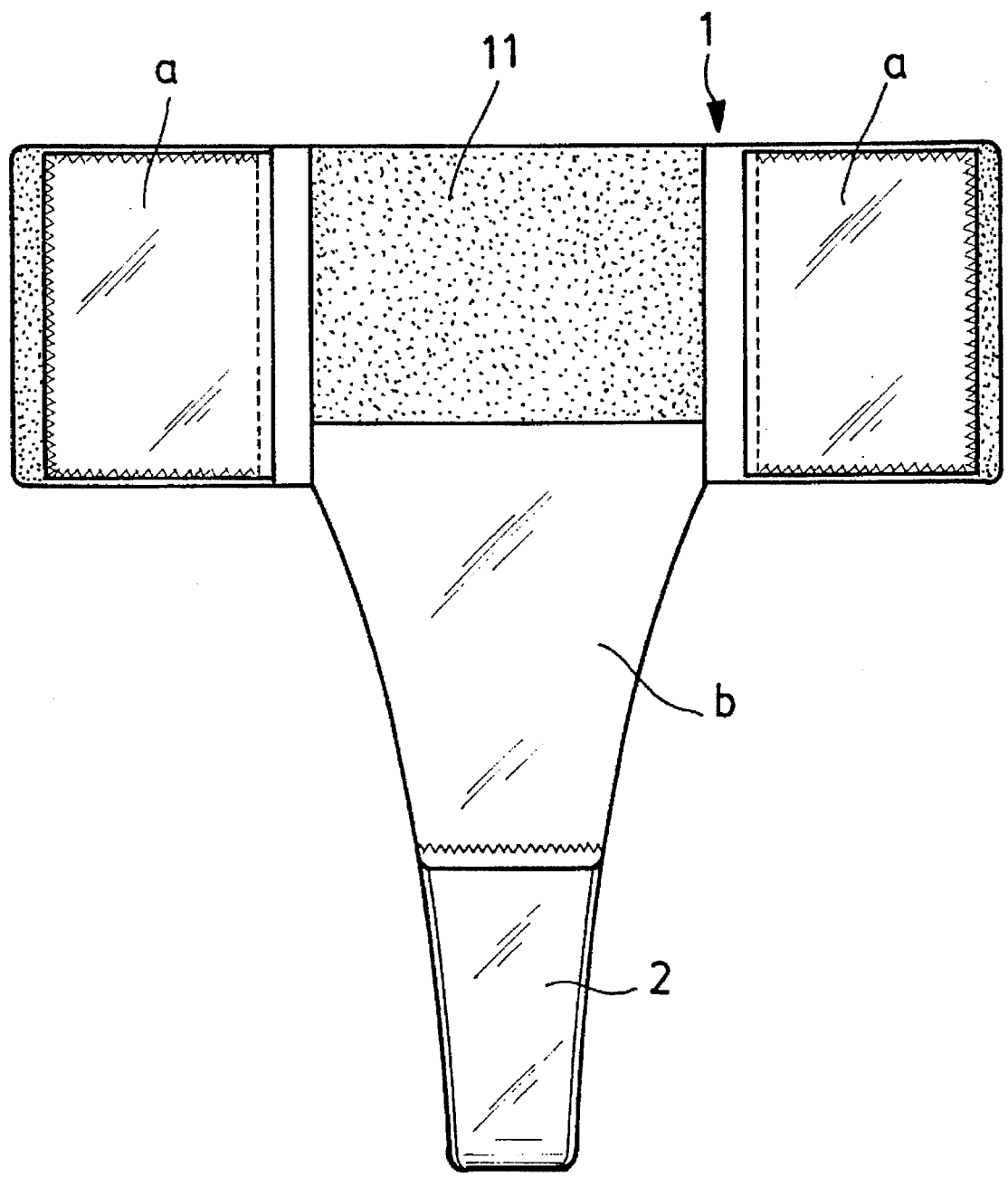
FIG. 5 is a rear elevational view of the jockstrap made according to the present invention.

Referring to FIGS. 2 to 5, the jockstrap made in accordance with the present invention comprises a waistband 1 made from soft material. A pouch portion 2 is attached to said waistband 1 and extends from the front portion to the rear portion of the waistband 1.

The rear portion of said waistband 1 is provided with a strap 11 having a hook-and-loop fastening system such as VELCRO, for readily adjusting the size of the waistband 1. A circular slot 21 is formed through the front portion of the pouch portion 2, in correspondence with the position of a user's penis. A tough seam 22 having a soft inner surface is formed between the slot 21 and the pouch portion 2. The rear portion of the pouch 2 is provided with an adjusting strap b which is also provided with a hook or loop fastener portion (not shown in FIG.) for cooperative coupling with a corresponding portion of strap 11.

By this arrangement, when a condom is worn by a male and the waistband 1, as well a the adjusting strap b, are well adjusted, the condom will be in intimate contact with the user's penis and the condom will not peel off during use.

On the other hand, the left and right side portions of said waistband 1 are also provided with adjusting straps a which also have hook or loop portions 12. The waistband 1 is also provided with a complementary loop or hook portion 13 for respective coupling with the portion 12.

In use, a male user first dons a condom 3 while his penis is erect. Them, he puts on the jockstrap to fix the condom. The condom sheathed penis readily passes through the circular slot 21 of the pouch portion 2. The circular portion of the slot 21 encloses the bottom 31 of the condom 3, as well as the root of the user's penis. By adjusting the adjusting strap b of the pouch portion 2, a compact and comfortable contact between the pouch portion 2 and the user's penis can be readily achieved. When the most comfortable position is achieved, the portion 11 can be used to fix the adjusting strap b. Meanwhile, the bottom 31 of the condom 3 is pressed against the root of the user's penis by the seam 22 surrounding the slot 21. By this arrangement, the condom and penis have intimate contact therebetween which will not be interrupted by the condom peeling off.

Figures 6, 6A:
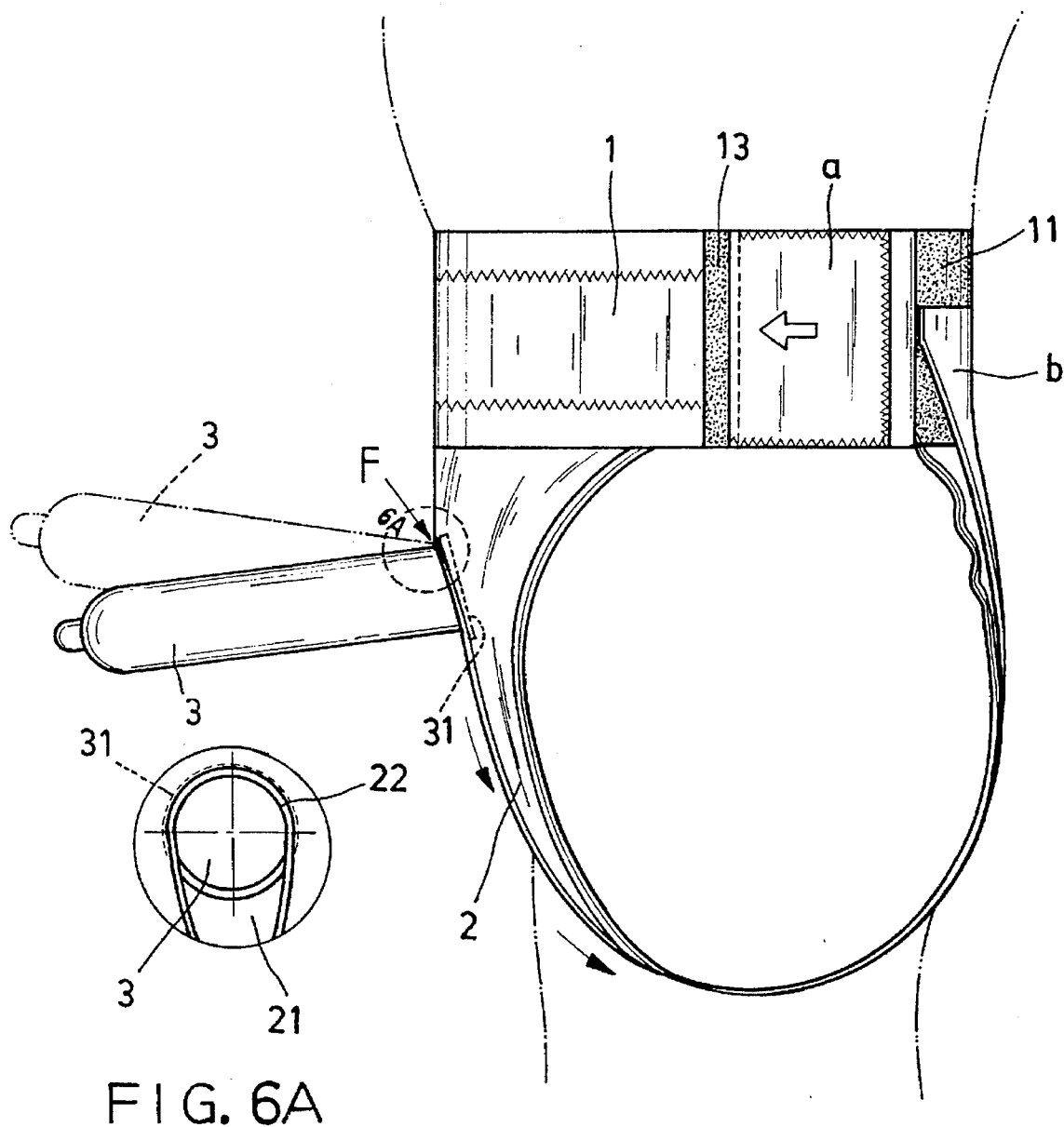
FIGS. 6 and 6A are illustrations showing a condom and the jockstrap of the present invention being worn by a male.

As shown in FIGS. 6 and 6A, by the engagement between the upper portion of adjusting strap b and the portion 11 of said waistband 1, the contraction force F, which is applied to the bottom 31 of the condom 3 by the circular slot 21, can be readily adjusted. Consequently, the contraction force presses the bottom 31 of the condom 3 against the root of the user's penis. By leverage, the erecting angle of the penis can be lifted upward, the corpus cavernosum of penis will more readily fill with blood, consequently, the erection and extension of the user's penis will become more complete.

Additionally, the respective portions 12 and 13 of the adjusting strap a and waistband 1 can be used to adjust the tightness of said waistband 1. Consequently, an excellent body contour can be achieved with the help of waistband of the jockstrap.

What the invention claimed is:

1. A jockstrap for fixing a condom in position on a user's penis, comprising:

a waistband made of a soft material, said waistband having a rear portion and a pair of side portions with respective hook and loop fastener portions; and a pouch portion having a front portion attached to said front portion of said waistband and extending to a rear portion attached to said rear portion of said waistband, said front portion of said pouch portion having a circular slot formed therethrough at a location in correspondence with a position of a user's penis, said front portion of said pouch portion having a tough seam surrounding said circular slot, said rear portion of said pouch portion having an adjusting strap adapted for releasable coupling with said hook and loop fastener portion of said rear portion of said waistband.

2. The jockstrap as recited in claim 1, wherein said waistband further comprises a pair of adjusting straps respectively disposed adjacent said pair of side portions of said waistband, each of said pair of adjusting straps being provided with a hook and loop fastener portion which is capable of engagement with said hook and loop fastener portion of a respective side portion of said waistband.

* * * * *